United States Patent [19]
Saferstein et al.

[11] Patent Number: 6,086,856
[45] Date of Patent: Jul. 11, 2000

[54] SYSTEM FOR DELIVERING FOAMED ORAL HYGIENE COMPOSITIONS

[75] Inventors: Albert Saferstein, Virginia Beach, Va.; Gary Gerard Fores, Sea Cliff, N.Y.

[73] Assignee: OralCare Systems, Inc., Virginia Beach, Va.

[21] Appl. No.: 08/530,078

[22] Filed: Sep. 19, 1995

Related U.S. Application Data

[63] Continuation-in-part of application No. 08/218,796, Mar. 28, 1994, Pat. No. 5,665,332.

[51] Int. Cl.[7] .............................. A61K 7/26; A61K 7/22; A61K 7/20; A61K 7/18
[52] U.S. Cl. ............................ 424/58; 424/49; 424/52; 424/53; 424/54; 424/55; 424/56; 424/45; 424/400
[58] Field of Search ........................ 424/400, 49, 44, 424/53, 56, 58, 616, 52, 54, 55, 45; 514/578

[56] References Cited

U.S. PATENT DOCUMENTS

| | | |
|---|---|---|
| 2,783,091 | 2/1957 | Haldy . |
| 4,511,486 | 4/1985 | Shah . |
| 4,522,806 | 6/1985 | Muhlemann et al. ............... 424/52 |
| 4,666,708 | 5/1987 | Goldemberg et al. ............... 424/49 |
| 4,836,422 | 6/1989 | Rosenberg .......................... 222/190 |
| 5,174,990 | 12/1992 | Douglas ............................... 424/49 |
| 5,369,131 | 11/1994 | Poli et al. ............................. 424/45 |

*Primary Examiner*—Thurman K. Page
*Assistant Examiner*—R. Bawa
*Attorney, Agent, or Firm*—Collard & Roe, P.C.

[57] ABSTRACT

Oral hygiene formulations comprising foaming surfactants are dispensed in the form of foams by means of an air-driven propellantless dispenser. The formulations comprise mouthwashes, rinses and dentifrices containing one or more antimicrobial anti-plaque and anti-cariogenic agents.

24 Claims, No Drawings

SYSTEM FOR DELIVERING FOAMED ORAL HYGIENE COMPOSITIONS

REFERENCE TO RELATED PATENT APPLICATION

This is a Continuation-In-Part patent application of U.S. patent application Ser. No. 08/218,796, filed Mar. 28, 1994, now U.S. Pat. No. 5,665,332.

BACKGROUND OF THE INVENTION

1. Field of the Invention

The present invention relates to an oral hygiene system comprising an oxygen-containing gas-driven, otherwise propellantless foam dispenser and a foamable oral hygiene formulation. More particularly, it relates to such system which is a personal self administrable oral hygiene system driven by air and producing aerated foams. The invention also relates to such an oral hygiene system driven by a high molecular oxygen content gas to be administered by mouth-care professionals.

2. The Prior Art

Formulations are known, many commercially available over-the-counter (OTC), for improving oral hygiene. Included are self-administrable OTC mouthwashes, rinses, gargles and dentrifices, as well as topical treatments to be administered by a trained professional. In general, the mouthwashes, rinses, gargles, and dentrifices for self-treatment are aqueous or aqueous alcoholic liquid solutions, pastes or gels incorporating one or more orally-acceptable antimicrobial, anti-plaque and/or anticariogenic agents, often in association with such auxiliary components as demulcents, mouth-wound cleansing and healing agents, astringents, analgesics, solution thickeners, sweeteners, flavorants, colorants and surfactants.

Representative liquid mouthcare formulations are disclosed in Talwar et al U.S. Pat. No. 4,945,087 relating to thymol-based antimicrobial mouthwashes and rinses; Goldemberg et al., U.S. Pat. No. 4,666,708 directed to plaque-loosening and removing alkaline dental rinses comprising sodium benzoate, a detergent builder and a surfactant; Douglas, U.S. Pat. No. 5,104,644 disclosing hydrogen peroxide-based anti-plaque and antibacterial mouthwashes; and Shah, U.S. Pat. No. 4,325,939 disclosing plaque-loosening rinses comprising zinc compositions.

The OTC liquid mouthwashes and rinses appear designed to provide effective daily oral care treatment with typical doses of about 0.5 to 1 fluid ounce (about 14 to 28 grams). The dose is to be intimately contacted with all surfaces of the oral cavity, as by swirling, for about 30 to 60 seconds; then expectorated substantially completely, without swallowing.

Many of the formulations and the method of self-treatment are not entirely satisfactory. Under the recommended conditions, much of the mouthcare material is considered wasted inasmuch as it is only that proportion of the dose that is at the outer surface of the body of liquid that is in direct interfacial contact at any one time with the target surfaces of the oral cavity. Thus, at the relatively short treatment times involved, a substantial proportion of the "actives", i.e., active ingredients, of the liquid dose remains in its interior out of contact with the target surfaces, hence unavailable for effective treatment, especially when the user fails to vigorously swish the material within the buccal cavity.

Another problem associated with the presence of excess amounts of liquid formulation in the mouth at any one time is that many of the ingredients are or believed to be harmful if ingested, e.g. fluorides, or maintained in contact with buccal tissues at high concentrations, e.g. alcohol, so that it is desirable to minimize the total amounts of such substances in the mouth during the treatment.

In view of the excess ingredient problem associated with fluoridating pastes and gels, Pellico, U.S. Pat. No. 4,770,634 discloses a fluoridating method, for use by dental professionals, which comprises treating teeth with foamed fluoride compositions. The method involves dispensing a foamable aqueous acid solution of a dental fluoride, a selected foaming agent and a foam wall thickener from a pressurized aerosol container by means of propane or isobutane as propellant. The formulation and the method of dispensing it are designed to provide dense, stable, non-flowable foams within the trough of a dental tray, which is superimposed about, and in engagement with the teeth to be treated for periods of 1 to 4 minutes, thereby to effect fluoride uptake by the dental enamel. Pellico teaches the benefit of limiting the total quantity of fluoride in the mouth during the treatment during the treatment period to safer levels than those provided by pastes and gels.

The Pellico system suffers in that it requires the aid of a third party and presents the hazard of handling a flammable gas maintained under super-atmospheric pressure. Thus, it is not entirely suitable for home use as a personal, self-administrable oral hygiene system.

Also known, in art unrelated to oral hygiene, are-driven, so-called propellantless devices for producing and dispensing foam that rely on the use of a reversibly compressible and decompressible container housing a foamable liquid and air normally at rest at substantially atmospheric pressure. Foam is produced by compressing, e.g. squeezing, the container, whereby the internal air pressure is increased sufficiently to force both liquid and air into a foam-producing mixing chamber and subsequently resulting in the expression of foam from the device. Allowing the container to decompress allows outside air to be drawn into the container through an appropriate valve and restore the system to its normal at rest, substantially atmospheric pressure, condition. Representative of such propellantless devices are those described in the following U.S. Patents: Wright U.S. Pat. No. 3,709,437; Kazuo U.S. Pat. Nos. 4,274,594 and 4,432,496; Grogan et al. U.S. Pat. No. 4,615,467; Ford et al. U.S. Pat. No. 4,640,440; Rosenberg U.S. Pat. No. 4,836,422; and Tobler U.S. Pat. No. 5,048,750. Collectively, these patents disclose that foam dispensers are useful for dispensing detergents, polishers, waxes, cosmetics, toiletries and foodstuffs. None disclose or suggest dispensing products relating to oral hygiene.

Poll et al, U.S. Pat. No. 5,369,131, issued Nov. 29, 1994, on a U.S. application filed May 20, 1993, discloses and claims liquid pharmaceutical compositions that are propellant free and mechanically foamable comprising at least one pharmaceutically active ingredient, a surfactant, a water-containing solvent, at least one of a mucoadhesive polymer and a thermosetting polymer. The foams may be used for oral, cutaneous or intravaginal administration. The surfactants may be ionic or preferably nonionic. Oral foams are intended to be ingested. Oral hygiene formulations are not disclosed.

A need exists for an improved system of dispensing foamed oral hygiene products simply and directly, efficiently and safely, to the oral cavity target areas, particularly such system suitable for self-treatment.

A need also exists for improved oral hygiene products that are foamable and dispensable by conventional gas-driven dispensers that avoid the use of environmentally objectionable gaseous chlorofluorocarbons (CFCs) and flammable hydrocarbons.

SUMMARY OF THE INVENTION

It is an object of the present invention to provide an oral hygiene system useful in the treatment and prevention of tooth decay, gingivitis and periodontal disease comprising a gas-driven foam dispenser housing a foamable aqueous oral hygiene formulation and a foam-producing gas comprising molecular oxygen, said gas being substantially free of CFC and hydrocarbon propellants.

In one aspect, the invention provides a personal self-administrable mouth care system wherein the foam dispenser is air-driven, that is, the foam-producing gas consists essentially of air and the foam produced is an aerated foam. Preferably, in this embodiment, the foam dispenser comprises a reversibly compressible and decompressible container housing, at substantially atmospheric pressure, said air and a foamable aqueous (including aqueous alcoholic) mouthcare formulation comprising one or more oral components and an orally-acceptable (hereinafter oral) surfactant as a foaming aid.

In another aspect, the invention provides an oral hygiene system for professional use wherein the foam dispenser is driven by a molecular oxygen-containing gas comprising from about 50 to 100 volume percent of molecular oxygen and from about 50 to 0 volume percent of an inert environmentally-acceptable and nonflammable gas, such as nitrogen, helium, argon, neon, carbon dioxide and mixtures of any two or more thereof.

In yet another aspect, the invention provides new, foamable mouthcare formulations, including mouthwashes, rinses and dentrifices as new compositions of matter that are foamable with air or other molecular-oxygen-containing gas.

In a further aspect, the invention comprises a process for treating the oral cavity with a mouthcare formulation, which comprises:

1. Bringing together, in foam-producing proportions, in a mixing zone,
   a. an aqueous mouthcare formulation containing a compatible oral surfactant in an effective foam-producing amount, and
   b. an oxygen-containing gas essentially free of environmentally-objectionable CFCs and flammable hydrocarbons;
2. causing said (a) and (b) components to mix such that they form an oxygenated (e.g. aerated) foam; and
3. Allowing the foam to be dispensed from the mixing zone, preferably directly into the oral cavity to be treated.

The mixing zone is conveniently the mixing chamber of a propellantless dispenser, more preferably such a device as described hereinafter.

Preferably, the formulation is non-ingestible and meant to be expectorated, the foaming gas is air, the surfactant is anionic, more preferably sodium lauryl sulfate (SLS).

It has been found that the delivery of oral hygiene components to the oral cavity in the form of a flowable foam improves the effervescence of the formulation and, in turn, improves the removal of tissue and other debris. The formulation is particularly well suited to suspend and foam away food particles and other debris, and then itself be rinsed away quickly.

The system of the present invention is capable of producing dramatic and rapid detergent action in order to instantly provide voluminous quantities of microbubbles from relatively small initial volumes of formulation. This detergent action, in turn, greatly facilitates the effectiveness of the formulation as an oral rinse. The invention system, for instance, can rapidly provide a volume of bubbles from about 2 grams of formulation that is as great or greater than the volume obtained by swirling up to an ounce (e.g., about 25–30 grams) of a commercial mouthwash in the mouth for 30 seconds, as recommended by the manufacturer.

The invention delivery system for mouthcare formulations may be a propellantless dispenser of the squeeze bottle variety. Such dispenser provides numerous advantages over the art, including simplicity, safety, efficiency and economy of operation. The foams are flowable and readily generated; for example, in the personal mouthcare embodiment, simply by squeezing the container and directing the resulting foam into the oral cavity as it is being dispensed for intimate contact with the oral target surfaces. The foam's effectiveness is aided by swishing the foam around in the mouth so that it can penetrate the interproximal spaces between adjacent teeth and between teeth and gums. In being foamed, the liquid formulation is transformed into an aerated low density mass comprising a multitude of bubbles comprising gas-supported thin-walled liquid films having a high surface area to liquid volume ratio. The foam thus presents a high concentration of actives at (or close to) the surface of the film for direct surface-to-surface contact with the target areas of the oral cavity. It is conjectured that actives leaving the surface of the film and adhering to the surface of the oral target are readily replaced at the surface, in view of the high surface area available, by diffusion of actives from within the liquid film to the surface thereof. Thus, the total amount of the liquid formulation needed for effective treatment may be greatly reduced, providing thereby economy at operation.

Further, since the aerated foams present a smaller total quantity of ingredients in the mouth at any one time during a given treatment period, and since many of the ingredients are harmful if ingested, the treatment with foam is inherently more safe than treatment with slugs of bulk liquid, in the event some of the material is inadvertently swallowed and ingested. It is recognized that swirling bulk liquid around in the mouth for 30 to 60 seconds may, in some cases, result in some foaming, however, the extent of such foaming is substantially less than that produced and provided in accordance with the compositional requirements and the method of this invention.

Also, in utilizing air or other molecular oxygen-containing gas, the invention treatment avoids the hazards, environmental objections and costs entailed in aerosol use of flammable hydrocarbons and environmentally-objectionable halocarbon propellants.

A further advantage is that the molecular oxygen-containing gas (supporting the liquid film of active ingredients of the foam) is also in position to contact the target surfaces of the oral cavity, in particular the gums. For example, by diffusion into and through the film or by breakdown of the bubbles under the swirling action of the mouth, the gas is available as a bactericide, alone or in conjunction with other antimicrobials normally present in the formulation.

The ratio of gas to liquid in the foams as dispensed can vary widely depending largely on (a) the surface tension of the liquid, which is a function of the surfactant it contains and its concentration (b) the actives and their concentrations in the liquid and (c) the desired effect. The gas/liquid ratio is conveniently expressed in terms of the relative densities of the foam (foamed liquid) and the bulk (unfoamed) liquid since the density of the foam is essentially determined by the weight of the liquid therein. In other words, the gas-liquid composition of the foam can be controlled by means of the surfactant to produce oral dosages that contain relatively small weight fractions of the liquid. Taking the density of the liquid equal to 1, typical such relative density fractions are in the range of from about $\frac{1}{3}$ to $\frac{1}{20}$ preferably $\frac{1}{4}$ to $\frac{1}{10}$. With such low usage of liquid in the foam, dosing the oral cavity may be repeated one or more times as needed to achieve a desired effect and still maintain a savings in liquid (i.e. actives) usage.

DETAILED DESCRIPTION OF THE PREFERRED EMBODIMENTS

The foam dispensing system of this invention comprises a foam dispenser driven by air, oxygen or other oxygen-containing environmentally-acceptable and non-flammable gas, in cooperative association with a foamable aqueous oral hygiene formulation containing an effective foam-producing amount of an oral surfactant.

Representative air-driven foam dispensers suitable for self-administering foamed formulations in accordance with the method of this invention are disclosed in the patents to Rosenberg, Wright, Kazuo, Ford et al., Grogan et al., and Tobler, all supra and hereby incorporated by reference. Included are devices designed for use in the upright or inverted position. All dispense foam in a propellantless manner in contrast to aerosol devices, which rely on a gaseous propellant initially pressurized within the device and maintained therein under pressure throughout its useful lifetime. The term "propellantless" manner used herein refers to the preparation and delivery of foam in a way that avoids use of an initially pressurized gas to achieve rapid expansion of the gas (propellant) through an emulsion. The devices used in the self-administrable embodiment of this invention are propellantless in the sense that they rely on air to produce an aerated foam. In one embodiment the air is initially incorporated into the device and maintained therein at substantially atmospheric pressure in a reversibly compressible and decompressible container. The air within the container can be brought to a state of increased pressure on demand, simply by compressing the container, e.g. by squeezing it, thereby providing sufficient driving force to produce and dispense foam from the device. The devices are also designed to have their air supply automatically replenished by allowing the container to decompress, whereupon air is drawn from the outside atmosphere into the container through a valve which is open to the atmosphere during the decompression mode but closed during the compression mode.

Typical of such propellantless foam dispensing devices are those of the above-referenced Tobler patent, for example, the device described with reference to FIG. 1 of the patent relating to an improved mounting section for the dispenser. The dispenser's compressible and decompressible container is conveniently composed of high density polyethylene or polypropylene.

Alternately, an outside source of pressurized gas may be used to provide and replenish the container's gas supply, particularly where the gas is oxygen diluted with up to 50% of a diluent gas as defined above. Also, conventional pressurized aerosol devices may be used with oxygen, or oxygen diluted as above, serving as the propellant under pressure.

The oral formulations that may be used in accordance with this invention include commercially available mouthwashes, rinses and dentrifices that either contain a sufficiency of a foam-promoting oral surfactant, or that are modified as exemplified hereinafter, to contain such sufficiency. Such sufficiency is readily determined by trial for any particular formulation without undue experimentation. The formulations normally comprise water or aqueous alcohol having up to about 25% ethanol, preferably less than 20%, as carrier solvent for one or more oral "actives," auxiliary components in minor amounts (including healing agents, demulcents, astringents, analgesics, sweeteners, solution thickeners, flavorants and colorants) and surfactants, preferably anionic, in foam-promoting amounts.

The "actives" comprise oral antimicrobial (including antibacterial, antifungal and antiseptic) agents, anti-plaque agents, and anti-carciogenic agents. Representative oral antimicrobials are: phenolics, such as phenol and thymol; carboxylic acids and alkali metal salts thereof, such as benzoic acid, sodium benzoate, sorbic acid and potassium sorbate; quaternary ammonium halides having antimicrobial properties such as cetylpyridinium chloride, domiphen bromide, benzalkonium chloride, cetalkonium chloride and benzethonium chloride; chlorhexidine; peroxides, notably hydrogen peroxide; zinc compounds, such as zinc chloride, zinc oxychloride, zinc hydroxide, zinc oxide, sodium zincate, zinc citrate, sodium zinc citrate and zinc fluoride; sodium salicylate; and compatible combinations thereof.

The concentration of the antimicrobial depends on the particular agent employed, and generally is in the range of from about 0.005% to about 3% by weight of the formulation, more usually in the range from about 0.01% to 1% by weight. For example, typical use ranges are: for thymol 0.01% to 1% by weight, preferably 0.02%–0.1% by weight as in U.S. Pat. No. 4,945,087; for sodium benzoate and sodium salicylate respectively, about 1% to 2% by weight and 0.1% to 1% by weight as in U.S. Pat. Nos. 4,657,758 and 4,666,708; for quaternary ammonium halide antiseptics about 0.005% to 2% by weight preferably 0.1% to 1% by weight; likewise for zinc-based antimicrobials it is normally 0.005% to 1% by weight as in U.S. Pat. Nos. 5,104,644 and 4,325,939; for hydrogen peroxide 0.1% to 3% by weight, more usually 0.25%–1.0% by weight as in U.S. Pat. Nos. 5,704,644 and 5,174,990. Those skilled in the art will recognize that many of the antimicrobials also exhibit anti-plaque activity, notably, sodium benzoate, the various zinc compounds and the quaternary ammoniums, the last named also capable of functioning as surfactants and as fluoride ion carriers for anticariogenic activity.

Preferably the antimicrobial agent is other than a peroxide. Hydrogen peroxide and other peroxides are susceptible to decomposition when in contact with various other substances.

Oral formulations incorporating anti-plaque agents that can be used herein are disclosed in U.S. Pat. No. 4,666,708. These comprise alkaline solutions containing at least about 1% by weight of sodium benzoate, as antimicrobial as well as anti-plaque agent; one or more detergent builders, e.g. sodium borate, sodium bicarbonate, sodium carbonate and/ or tetrasodium pyrophosphate, in amounts sufficient to provide pH 7.5 to 10, preferably pH 7.5 to 9; and an anionic surfactant such as sodium lauryl sulfate in amounts sufficient to produce a desired foaming effect, readily determinable by trial and generally in the 0.05% to 1.5% by weight range. Other oral anti-plaque compounds and formulations that may be used herein are disclosed in U.S. Pat. No. 4,522,806 and U.S. Pat. No. 4,325,939.

Anticariogenic formulations that may be employed include dental fluoridators such as sodium, potassium and ammonium fluoride, sodium monofluoro phosphate, stannous fluoride, zinc fluoride and dodecyltrimethyl ammonium fluoride among others known to the art, and mixtures thereof, generally in amounts sufficient to release from about 0.01% to about 0.05% fluoride by weight of the formulation for self-administered use as utilized, for example, in various OTC formulations, and up to about 5 weight % of available fluoride, as disclosed in U.S. Pat. No. 4,770,634 for professionally administered care.

The oral surfactant herein is preferably ionic, more preferably anionic, alone or in combination with a compatible nonionic surfactant. However, when the antimicrobial is a quaternary ammonium halide the surfactant normally is cationic or a mixture thereof with a nonionic surfactant. Highly preferred are alkali metal long-chain alkylsulfates, where the alkyl group has 9 to 15 carbon atoms, preferably for reasons of availability and effectiveness, sodium lauryl sulfate, commonly known in the art as SLS, which is generally used in amounts from about 0.05% to 2% by weight, preferably 0.1% to 1.5% by weight. Other suitable oral anionic surfactants that may be used in substantially similar amounts are sodium dodecylbenzene sulfonate, sodium cocomonoglyceride sulfonate, sodium lauroylsarcosinate, and the like, potassium and triethanolammonium sulfates, sulfonates and sarcosinates.

The anionic surfactants are often advantageously employed with oral nonionic surfactants, notably poly (oxyethylene)—poly (oxypropylene) block copolymers, known as poloxamers, produced in a wide range of structures and molecular weights from varying proportions of ethylene oxide and propylene oxide. Examples are the poloxamers designated 331 and 407 sold under the trademark PLURONIC-F-101® and PLURONIC-F-127®, respectively, available from BASF Wyandotte Co., Wyandotte, Mich. Other useful nonionics include mixtures of laurate esters of sorbitol and of sorbitol anhydrides consisting predominately of the monoester condensed with about 15 to 25 molar proportions of ethylene oxide, more specifically, such product commonly known as Polysorbate 80 and available under the trademark TWEEN 20® from I.C.I. Americas, Wilmington, Del.

All percents by weight for all additives such as the antimicrobial agents, the anti-plaque agents, the anticariogenic agents, and the surfactants are based upon the total composition weight.

As already noted, the art recognizes that the cationic oral quaternary ammonium halide antimicrobials, such as cetylpyridinium chloride and domiphen bromide, employed in several OTC mouthwashes, and the known anticariogenic agent cetyltrimethyl ammonium fluoride, also exhibit surfactant properties. For the purpose of providing surfactancy as well as their other functions, such cationics ar preferably used herein at the high end of their normal 0.005% to 1% by weight use range.

Typical auxiliary components, recognized and utilized in the art, include: humectants and demulcents (glycerol, propylene glycol, sorbitol); sweeteners (sodium saccharin and "sugar alcohols," e.g. sorbitol, xylitol, mannitol, maltitol, hydrogenated starch hydrolysate); flavorants (saccharin, eucalyptol, anethole, menthol, methyl salicylate); wound healer (allantoin); anti-inflammatory steroids, (Eisen U.S. Pat. No. 5,407,663); alkalizers and detergent builders (sodium hydroxide, sodium carbonate, sodium borate, mono- and disodium phosphate, tetrasodium pyrophosphate); buffering agents (sodium bicarbonate); sequestrants (ethylenediaminotetraacetic acid, citric acid); analgesics (sodium salicylate); anticoagulants (sodium citrate); thickening agents/viscosity builders (water-soluble polyethylene glycols, $H(OCH_2CH_2)_nOH$, where n is greater than 4, xanthan gum, carrageenan and other hydrocolloids).

Preferred for foaming purposes are oral formulations whose surface tensions are below about 30 dynes/cm at 20° C., preferably from about 10 to 25 dynes/cm. Preferably, too, the formulations will exhibit viscosities at ambient temperatures sufficiently low to result in flowable and readily expectoratable foams. Suitable combinations of surface tensions and viscosities are readily determined by trial, e.g. by adjusting surfactant and solution thickener contents, using standard methods without undue experimentation.

Typically, the foamable aqueous (including aqueous alcoholic) oral formulation comprises about 70% to 98% by weight of the carrier solvent and 30% to 2% by weight of the additives. All percents by weight are based upon the total formulation weight.

An important feature of the invention is that the oxygen gas, component of the foamed formulation, which is a known anaerobic bactericide (U.S. Pat. No. 5,104,644, col. 7) can be brought into cooperative, intimate contact with the oral target areas along with other actives of the formulation, for example, by vigorously swishing the foam throughout the oral cavity. It is believed such action helps effect therapeutic contact of the foam as a totality with the teeth and gums. Thus, the gas as a whole can serve as a means of foaming away food particles and other debris while its oxygen component can function as an active bactericide, the higher its concentration in the gas, the greater its potential bactericidal effect.

The foamed dentifrice embodiment includes non-abrasive and abrasive formulations. In general, any of the above-described foamable oral hygiene formulations may serve as foamed dentifrices as well as mouthwashes and rinses, with or without an abrasive such as hydrated silica incorporated therein. A typical foamed abrasive dentifrice of this invention may contain in weight %: a fluoridating agent, e.g. sodium fluoride (0.1 to 0.3); hydrated silica (1 to 3); a demulcent such as glycerol and/or sorbitol (10 to 25); and one or more of potassium sorbate, sodium benzoate or other antimicrobial agents (0.1 to 0.5); an alkalizer and anti-plaque adjuvant, e.g. tetrasodium pyrophosphate (0.1 to 1); a thickener such as xanthan gum, carrageenan and/or a polyethylene glycol, e.g. PEG 400–600 (0.03 to 1); a sweetener such as sodium saccharin (0.01 to 0.03); SLS (0.3 to 1.5); flavorant (to taste); deionized water, with or without ethanol, (to 100). The dentifrice may also contain up to 5% of densitizer such as potassium nitrate or strontium chloride to protect against sensitivity of the teeth to heat, cold, acids, and painful brushing contact.

Foamed dentifrices made in accordance with the invention may be used with electrically-driven as well as conventional manually operated toothbrushes, an advantage over regular toothpastes and gels which tend to clog electric brushers.

In formulating an abrasive dentifrice and selecting a foam dispenser for it, it is advisable to coordinate the dental composition, in particular the particle size of the abrasive and the fluidity of the mixture of ingredients with the structure of the mixing element of the dispenser, which may include, for example, a pervious fine mesh sieve or an open-pore rigid foam piece of plastic or ceramic material to achieve better mixing of the formulation with air before full foaming, so as to avoid clogging the mixing element in use. The higher the mesh count of the sieve, (or the smaller the pore size of the rigid foam piece) the smaller should be the particle size of the abrasive.

Those skilled in the art will appreciate that the carrier solvents composed of water and water containing minor proportions of alcohol as defined herein are dissociating solvents wherein dissociable ionizable compounds such as carboxylic acids and their alkali metal salts, quaternary ammonium halides, inorganic halides in general and other ionic compounds are at least in part dissociated into positive and negative ions in equilibrium with undissociated molecules, which may be the same or different molecules depending on the number of different dissociable molecules originally added to the solvent. Thus, for example, dissolving zinc chloride and sodium citrate in an alkaline aqueous dissociating medium would result in the formation of divalent zinc cations, monovalent zinc chloride cations, monovalent zinc hydroxide cations, sodium cations and citrate anions, both mono-and divalent, among other dissociated and undissociated chemical moieties and compounds. Thus, it will be also appreciated by those skilled in the art that essentially the same solution could be achieved by dissolving appropriate proportions of sodium chloride and zinc citrate in the original solvent. It should therefore be apparent that many of the ingredients employed in creating the foamable formulations are normally and conveniently selected on the basis of their availability, cost, safety in handling, and having been previously approved as "orally-acceptable" for the intended purpose.

Other objects and features of the present invention will become apparent from the following Examples, which disclose the preferred embodiments of the present invention. It should be understood, however, that the Examples are designed for the purpose of illustration only and not as a definition of the limits of the invention.

EXAMPLE 1

To a commercial-type thymol-based mouth rinse formulation having the composition given below in weight % is added pharmaceutical grade sodium lauryl sulfate (STEPANOL WA-100®), Stephan Co., Northfield, Ill. 60093) in an amount sufficient to provide about 0.2 weight percent of the total composition. The resulting solution is loaded into a foam dispenser designated (A) of the type described in Tobler, U.S. Pat. No. 5,048,750 for dispensing foam in the upright position, more particularly with reference to FIG. 1 therein so that the cylindrical compressible-decompressible high density polyethylene container (1½" diameter by 4½" tall) has about 80% of its volume occupied by the liquid formulation; the rest, above the liquid level, occupied by air.

The Formulation

| Ingredient | Weight % |
|---|---|
| Thymol | 0.06 |
| Sorbitol | 30 |
| Anethole | 0.02 |
| Eucalyptol | 0.08 |
| Menthol | 0.05 |
| Methyl Salicylate | 0.05 |
| Ethanol | 23 |
| Benzoic Acid | 0.15 |
| Sodium Saccharin | 0.03 |
| Sodium Citrate | 0.03 |
| Citric Acid | 0.01 |

-continued

The Formulation

| Ingredient | Weight % |
|---|---|
| Poloxamer 407 | 0.50 |
| Water | to 100% |

An untreated substantially equal volume sample of the undoped formulation of Example 1 is likewise loaded into an identical dispenser (B) of the same type, as a control.

Squeezing container (A) one or more times allowing the bottle to decompress after each squeezing, produces with each squeeze a voluminous foam which may be self-administered as a germicidal mouthwash. In contrast, under the same conditions, the control solution in container (B) produces little or no foam.

Further, dispensing Example 1 foam into and filling a tared vessel with it shows the vessel is filled with less than about 10 g of foam compared to 60 g of the Example 1 unfoamed liquid formulation required to fill it.

EXAMPLE 2

An anti-plaque dental rinse similar to that described in Example 4 of U.S. Pat. No. 4,666,708 is formulated from the following components combined in the weight percentages tabulated below:

| Weight % | Component |
|---|---|
| 2.0 | Sodium benzoate |
| 0.2 | Sodium salicylate |
| 0.5 | Sodium Bicarbonate |
| 0.2 | Sodium Borate |
| 0.5 | Sodium lauryl sulfate |
| 0.8 | Polysorbate 20 |
| 0.02 | Sodium saccharin |
| 15.0 | Glycerol |
| 7.0 | Ethanol, 95% |
| qs | Water to 100% |

Dispensing the formulation from a Tobler, U.S. Pat. No. 5,048,750 device similar to that described in Example 1 yields a voluminous foam having a high air to liquid volume ratio, self-administrable as a swishable dental rinse.

EXAMPLE 3

(A). An anti-plaque dental rinse having the composition tabulated below is formulated in the manner described in Example 1 of U.S. Pat. No. 4,666,708 except that sodium lauryl sulfate is also added as given below:

The Formulation

| Ingredient | Weight % |
|---|---|
| Sodium benzoate | 2.00 |
| Sodium bicarbonate | 0.50 |
| Sodium borate | 0.20 |
| Sodium salicylate | 0.20 |
| Allantoin | 0.20 |
| Xanthan gum | 0.03 |
| Glycerin | 15.50 |
| Ethanol | 6.60 |

-continued

| Ingredient | Weight % |
| --- | --- |
| Polysorbate 20 | 0.84 |
| Flavor | 0.31 |
| 1% FDC Red 40 | 0.8 |
| Sodium lauryl sulfate | 1.0 |
| Water to 100% | |

The Formulation

This formulation, in view of its glycerin, polysorbate 20 and xanthan gum content, forms a viscous foam having a high air-to-liquid volume ratio when dispensed as described in Examples 1 and 2 above. The dispensed foam is suitable for self-administration of the anti-plaque formulation.

(B). Substantially the same results are obtained by employing (a) "Plax" Advanced Formula, Soft MINT Flavor, an over-the-counter product of Pfizer, Inc., New York, N.Y. or (b) the same formulation without xanthan gum in place of the formulation described above.

EXAMPLE 4

To the formulation of Example 2 are added sodium fluoride, sodium citrate, citric acid and zinc chloride in amounts providing 0.02, 0.04, 0.02, and 0.03 weight percent, respectively. The resulting formulation may be self-administered as an anti-plaque and dental fluoridating foam dispensed as described in Example 1.

EXAMPLE 5

A hydrogen peroxide ($H_2O_2$)-based aqueous mouthwash comprising 0.60% $H_2O_2$, 0.02% zinc chloride, 0.03% sodium citrate, 0.02% citric acid and 0.2% sodium lauryl sulfate, all in weight percent, is prepared as described in Example 2 of U.S. Pat. No. 5,174,990 using the method of Example 1 of the patent. The ingredients and their concentrations are substantially as given in column 6 of the patent except that the concentration of the sodium lauryl sulfate is increased from 0.06% to that recited above. The resulting formulation is self-administrable in accordance with the present invention for the purpose of oral therapy and the prevention of dental disease disclosed in U.S. Pat. No. 5,174,990 above.

EXAMPLE 6 (A,B,C)

(A). The procedure of Example 1 is repeated employing a purchased OTC mouthwash, namely LISTERMINT® Mouthwash with Fluoride, a product of Warner-Lambert Co., Morris Plains, N.J.; except no SLS was added since this substance is listed as an ingredient in the mouthwash. The OTC product yields a voluminous foam on being dispensed as described in the referenced example.

(B). Substantially similar results are obtained as in (A) above using, as purchased, "ORAL PURE" Anti-Plaque Dental Rinse Plus Fluoride, also containing SLS, produced for KMart Corp., Troy, Mich.

(C). Substantially similar results are obtained in the procedure of Example 1 on employing, as purchased, OTC LAVORIS® Dental Rinse and adding to it an effective foaming amount of SLS. The undoped formulation, represented on the label as containing water, ethanol (as SD alcohol 38-B), glycerin, poloxamer 407, polysorbate 80, peppermint oil, sodium hydroxide, citric acid, zinc oxide and FD&C Blue #1, is essentially non-foamable.

EXAMPLE 7

This example illustrates the effectiveness of the invention system to produce functional foams from three different OTC mouthwash formulations incorporating cetylpyridinium chloride and domiphen bromide as actives, namely: (A) SCOPE® Clean Mint Mouthwash and Gargle, with baking soda, made by Proctor and Gamble, Cincinnati, Ohio; (B) "Oral Pure" Mint Mouthwash and Gargle, made for KMart Corp., Troy, Mich; and (C) "Lander" Refreshing Mint Mouthwash and Gargle, sold by Lander Co., Inc., Englewood, N.J.

Satisfactory foams are obtained employing the procedure of Example 1 above.

EXAMPLE 8

The system is well-suited for the delivery of non-ingestible expectoratable formulations to the oral cavity as medicaments. When used for cleansing minor wounds or irritations of the mouth or gums, for example, a small amount of the medicated, e.g. $H_2O_2$-containing foam is dispensed and applied to the affected area. It is allowed to remain in place for about one minute, and then expectorated. The foam can be used up to four times daily (after meals and at bedtime) or as directed by a dentist or physician. Children younger than 12 years of age should be supervised by an adult in the use of the foam, and for children younger than 2 years of age, a dentist or physician should be consulted prior to use.

The present invention has been described with reference to various embodiments thereof. It will be apparent to those skilled in the art that many changes can be made in the embodiments described without departing from the scope of the present invention. Thus, the scope of the present invention should not be limited to the formulations described in this application, but only by formulations described by the language of the claims and the equivalents of those formulations.

What is claimed is:

1. A self-administrable oral hygiene system comprising an air-driven foam dispenser comprising a reversibly compressible and decompressible container housing separate volumes of (i) a foamable aqueous mouthwash comprising one or more compatible foam-promoting oral surfactants and, in effective hygienic amounts, at least one agent selected from the group consisting of an oral antimicrobial agent, an anti-plaque agent, an anticariogenic agent and mixtures thereof, said agent being soluble or dispersible in water or water containing up to about 25% of ethanol and, (ii) a foam-producing amount of air.

2. An oral hygiene system comprising a gas-driven foam dispenser housing (i) a foamable aqueous oral hygiene formulation incorporating a compatible oral surfactant and, in effective hygienic amounts, at least one agent selected from the group consisting of an oral antimicrobial agent, an anti-plaque agent, and anticariogenic agent, and the mixtures thereof, said agent being soluble or dispersible in water or water containing up to about 25% of ethanol, and (ii) an environmentally-acceptable and non-flammable gas comprising molecular oxygen, said gas and surfactant being present in effective foaming amounts.

3. The system of claim 1,
wherein the gas comprises air substantially free of chlorofluorocarbon and hydrocarbon propellants.

4. The system of claim 2, further comprising a mouthwash.

5. The system of claim 4,
wherein the mouthwash additionally includes at least one orally acceptable and compatible agent selected from the group consisting of demulcents, sweeteners, astringents, analgesics, alkalizers, wound healing agents, anti-inflammatory steroids, hydrocolloids, chelating agents, pH-bufferers, colorants and mixtures of any two or more thereof.

6. The system of claim 4,
wherein the oral-antimicrobial agent is selected from the group consisting of thymol, a quaternary ammonium halide, benzoic acid, an alkali metal benzoate, sorbic acid, an alkali metal sorbate, chlorohexidine, hydrogen peroxide, an oral dentally-acceptable zinc compound and compatible mixtures of any two or more thereof.

7. The system of claim 6,
wherein the oral surfactant is anionic or cationic with the proviso that when the antimicrobial agent is a quaternary ammonium halide the surfactant is cationic or a mixture thereof with a nonionic surfactant.

8. The system of claim 6, wherein
(a) the antimicrobial agent comprises an effective amount of thymol;
(b) the mouthwash further comprises effective thymol-taste-masking amounts of a sugar alcohol and anethole; and
(c) the surfactant comprises an oral anionic surfactant or a mixture thereof with an oral nonionic surfactant in a foam-promoting minor amount.

9. The system of claim 8,
wherein the anionic surfactant is sodium laurylsulfate.

10. The system of claim 9,
wherein the formulation further includes a minor effective amount of a nonionic surfactant.

11. The system of claim 4,
wherein the antimicrobial agent is a quaternary ammonium halide.

12. The system of claim 11,
wherein the quaternary ammonium halide comprises cetylpyridinium chloride, domiphen bromide or a mixture thereof, said quaternary ammonium halide providing surfactant properties sufficient for foaming as well as antimicrobial properties.

13. The system of claim 4,
wherein the oral hygienic component comprises an agent selected from the group consisting of an antimicrobial agent, an anti-plaque agent, and the mixtures thereof, and is one or more of benzoic acid, sodium benzoate and an oral dentally-acceptable zinc compound.

14. The system of claim 13,
wherein the mouthwash containing said hygienic component has a pH of from about 7 to about 10.

15. The system of claim 14, wherein
(a) the antimicrobial and anti-plaque agent comprises sodium benzoate at a concentration of at least about 1 weight % of the mouthwash; and
(b) the mouthwash further comprises an alkaline detergent builder and an anionic surfactant, and has a pH of from about 7.5 to 9.

16. The system of claim 15,
wherein the anionic surfactant is sodium laurylsulfate.

17. The system of claim 15,
wherein the mouthwash further includes an anticariogenic agent comprising a dentally-acceptable fluoride soluble therein.

18. The system of claim 15,
wherein the antimicrobial and anti-plaque mouthwash further comprises: one or more orally-and-dentally-acceptable zinc compounds, and one or more of sodium citrate and citric acid.

19. The system of claim 4,
wherein the oral hygienic component comprises an anticariogenic agent comprising a dentally-acceptable fluoride soluble in said mouthwash.

20. The system of claim 4,
wherein the antimicrobial component comprises hydrogen peroxide; and
the mouthwash has a pH from about 3 to 7 and contains: (a) one or more oral dentally-acceptable zinc compounds, (b) one or more of sodium citrate and citric acid, and (c) a compatible anionic surfactant.

21. A kit for delivering a foamable oral hygiene formulation of claim 2 in the form of a foam, the kit comprising a propellantless dispenser and a separately packaged volume of said foamable formulation.

22. A self-administrable tooth cleansing system, comprising an air-driven foam dispenser housing separate volumes of a foamably dispensable aqueous dentifrice formulation containing an abrasive component and, in effective hygienic amounts, at least one agent selected from the group consisting of an oral antimicrobial agent, an anti-plaque agent, an anticariogenic agent and mixtures thereof, said agent being soluble or dispersible in water or water containing up to about 25% of ethanol, and a foaming amount of air.

23. An oral hygiene system comprising a gas-driven foam dispenser housing
(i) a foamable aqueous oral hygiene formulation incorporating a compatible oral surfactant and, in effective hygienic amounts, at least one agent selected from the group consisting of an oral antimicrobial agent, an anti-plague agent, and anticariogenic agent and the mixtures thereof, said agent being soluble or dispersible in water or water containing up to about 25% of ethanol, and
(ii) an environmentally-acceptable and non-flammable gas wherein the gas comprises from about 50 to 100% by volume of molecular oxygen and from about 50 to 0% of an inert environmentally-friendly and non-flammable gas, said gas and surfactant being present in effective foaming amounts.

24. A kit for delivering a foamable oral hygiene formulation of claim 1 in the form of a foam, the kit comprising a propellantless dispenser and a separately packaged volume of said foamable formulation.

* * * * *